United States Patent [19]

Nishida

[11] Patent Number: 5,691,481

[45] Date of Patent: Nov. 25, 1997

[54] METHOD AND APPARATUS FOR OBTAINING DATA ON THE STRAIN-STRESS RELATION OF TEST PIECES OF GREEN SAND MOLDS

[75] Inventor: Tadashi Nishida, Toyokawa, Japan

[73] Assignee: Sintokogio, Ltd., Japan

[21] Appl. No.: 565,849

[22] Filed: Dec. 1, 1995

[30] Foreign Application Priority Data

Dec. 2, 1994 [JP] Japan .................. 6-329594

[51] Int. Cl.$^6$ .................. G01D 1/16; G01D 7/02
[52] U.S. Cl. .................. 73/790; 73/789
[58] Field of Search .................. 73/760, 788, 789, 73/790, 791, 818

[56] References Cited

U.S. PATENT DOCUMENTS

| | | | |
|---|---|---|---|
| 2,645,151 | 7/1953 | Hastings et al. | 73/791 |
| 3,003,351 | 10/1961 | Ziegler et al. | 73/791 |
| 3,826,902 | 7/1974 | Claxton et al. | 73/789 |
| 4,802,367 | 2/1989 | Petersen et al. | 73/805 |
| 5,090,249 | 2/1992 | Beilewicz | 73/822 |
| 5,379,235 | 1/1995 | Fisher et al. | 73/789 |
| 5,396,804 | 3/1995 | Moet et al. | 73/789 |

*Primary Examiner*—Richard Chilcot
*Assistant Examiner*—Max H. Noori
*Attorney, Agent, or Firm*—Limbach & Limbach LLP

[57] ABSTRACT

A method is disclosed for obtaining data on the strain-stress relation of a test piece of molding sand under a varying load to predict the degree of deformation of a green sand mold which is caused after the green sand mold is moved or filled with molten metal. The test piece of molding sand for a green sand mold is produced by compressing the molding sand. The varying load, and varying length of the test piece under the varying load, are measured at short intervals. Based on the measurements, the strain-stress relation of the test piece is calculated and then the data is stored. The stored data is used to predict the degree of deformation of a green sand mold produced from the same molding sand that is tested.

1 Claim, 7 Drawing Sheets

METHOD AND APPARATUS FOR OBTAINING DATA ON THE STRAIN-STRESS RELATION OF TEST PIECES OF GREEN SAND MOLDS

FIELD OF THE INVENTION

This invention relates to a method and an apparatus for determining the strain-stress relation of a test piece of a green sand mold, and in particular to a method and an apparatus for determining the strain-stress relation of a test piece of a green sand mold to predict the degree of deformation of the green sand mold subjected to compressive, tensile, and shear stresses wherein the test piece is obtained by compressing molding sand, which is used to produce a green sand mold, under conditions approximating those for actually producing a given green sand mold.

DESCRIPTION OF THE PRIOR ART

Recently, for making mold products thin and light and reducing the steps in producing them, products of accurate dimensions have been required. Accordingly, not only must accurate dimensions for the cavity of a green sand mold in which molten metal is east be made, but also the deformation of the green sand mold must be prevented, particularly when it is moved or filled with molten metal.

However, conventionally, no latent deformation of the green sand mold after being moved or filled with molten metal has been given any attention at all, but only the hardness or strength of the green sand mold or the compactability or air permeability of the molding sand was measured. Further, causes of the deformation of the cavity of the mold when it is moved or filled with molten metal, which impairs the accuracy of the dimensions of the products, have not been studied. As a result of the inventor's study of the properties of molding sand for green sand molds, he was able to find the causes.

SUMMARY OF THE INVENTION

The present invention was made because of the circumstances mentioned above, and aims to provide a method and apparatus for obtaining data on the strain-stress relation of a test piece to predict the deformation of the green sand mold, which is caused after it is moved or filled with molten metal, wherein the test piece is obtained by compressing molding sand, which is used to produce a green sand mold, under conditions approximating those for actually producing a given green sand mold.

To achieve the purpose as mentioned above, in one aspect as shown in FIG. 1, this invention provides a method to obtain the data on the strain-stress relation of a test piece to predict the degree of deformation of a green sand mold wherein the test piece is obtained by compressing molding sand, which is used to produce a green sand mold, under conditions approximating those for actually producing the given green sand mold, characterized in that the method includes the steps of putting on the test piece an incrementally varying load along with the lapse of time (block 21 in FIG. 1), measuring the varying load and the varying length of the test piece under the varying load at short intervals (block 22), calculating the strain-stress relation of the test piece based on the measurements at such intervals, and storing the data on the calculated strain-stress relation (block 23).

In the present invention the strains include compressive, tensile, and shearing strains, and the stresses include compressive, tensile, and shearing stresses.

To achieve the purpose as mentioned above, in another aspect, as shown in FIG. 2, this invention provides an apparatus for obtaining the data on the strain-stress relation of a test piece to predict the degree of deformation of a green sand mold wherein the test piece is obtained by compressing molding sand, which is used to produce a green sand mold, under conditions approximating those for actually producing the given green sand mold, characterized in that the apparatus includes a first supporting member 1 to support one end of the test piece, a second supporting member 2 to support the other end of the test piece supported by the first supporting member 1, a servomotor 4 to put an incrementally varying load over time on at least one of the first and second members 1, 2 by a ball screw 3 wherein the movement of the screw is converted from a rotational to a linear one, torque-instruction means 5 for sending instructions to the servomotor 4 so that it outputs a torque, length-measuring means 6 for measuring a varying length of the test piece at short intervals, calculating means 7 for calculating the strain-stress relation of the test piece at the short intervals based on the measurements by the length-measuring means 6 and on the torque value given by the torque-instruction means 5, and memory means 8 for storing the results calculated by the calculating means 7.

In the configuration of the apparatus of this invention, the servomotor 4 is driven by the torque-instruction means 5 to advance or retract the ball screw to compress or pull the test piece. The variation of the length of the test piece is measured over time by the measuring means 6 at short intervals. The strain-stress relation of the test piece measured at intervals is then calculated by the calculating means 7, and the data on the results calculated is stored in the memory means 8. Since the properties of the green sand mold produced from the molding sand are obtained by using the data in the memory mean, the degree of the deformation can be predicted due to the movement of the green sand mold or filling it with molten metal.

Further, to achieve the purpose as mentioned above, in a further aspect of this invention, as shown in FIG. 3, it provides an apparatus for obtaining the data on the strain-stress relation of a test piece to predict the degree of deformation of a green sand mold wherein the test piece is obtained by compressing molding sand, which is used to produce a green sand mold, under conditions approximating those for actually producing a given green sand mold, characterized in that the apparatus includes a first supporting member 1 to support one end of the test piece, a second supporting member 2 to support the other end of the test piece supported by the first supporting member 1, a servomotor 4 to put an incrementally varying load over time on at least one of the first and second members 1, 2 by a ball screw 3 wherein the movement of the screw is converted from a rotational to a linear one, load-measuring means 9 for measuring at short intervals the varying load put on the test piece, length-measuring means 6 for measuring the varying length of the test piece at the such short intervals, calculating means 7 for calculating the strain-stress relation of the test piece measured at such short intervals based on the measurements by the length-measuring means 6 and the load-measuring means 5, and memory means 8 for storing the calculated results by the calculating means 7 at such short intervals.

In the configuration of the apparatus of this aspect of the invention, the servomotor 4 is driven to advance or retract the ball screw to compress, pull, or shear the test piece. The variation in the deformation of the test piece is measured over time by the measuring means 6 at short intervals. The varying load put on the test piece is measured at such short intervals by the load-measuring means 9. Further, the strain-stress relation of the test piece at such short intervals is calculated by the calculating means 7, and the data on the results calculated is stored in the memory means 8. Since the properties of the green sand mold produced from the molding sand are obtained by using the data in the memory means, the degree of the deformation of the green sand mold due to its movement or filling it with molten metal can be predicted. When designing a pattern plate, the designer can feed back this predicted deformation information to design the pattern plate to prevent deformation when a green sand mold is removed from the pattern plate.

DESCRIPTION OF THE PREFERRED EMBODIMENTS

Figure 1:
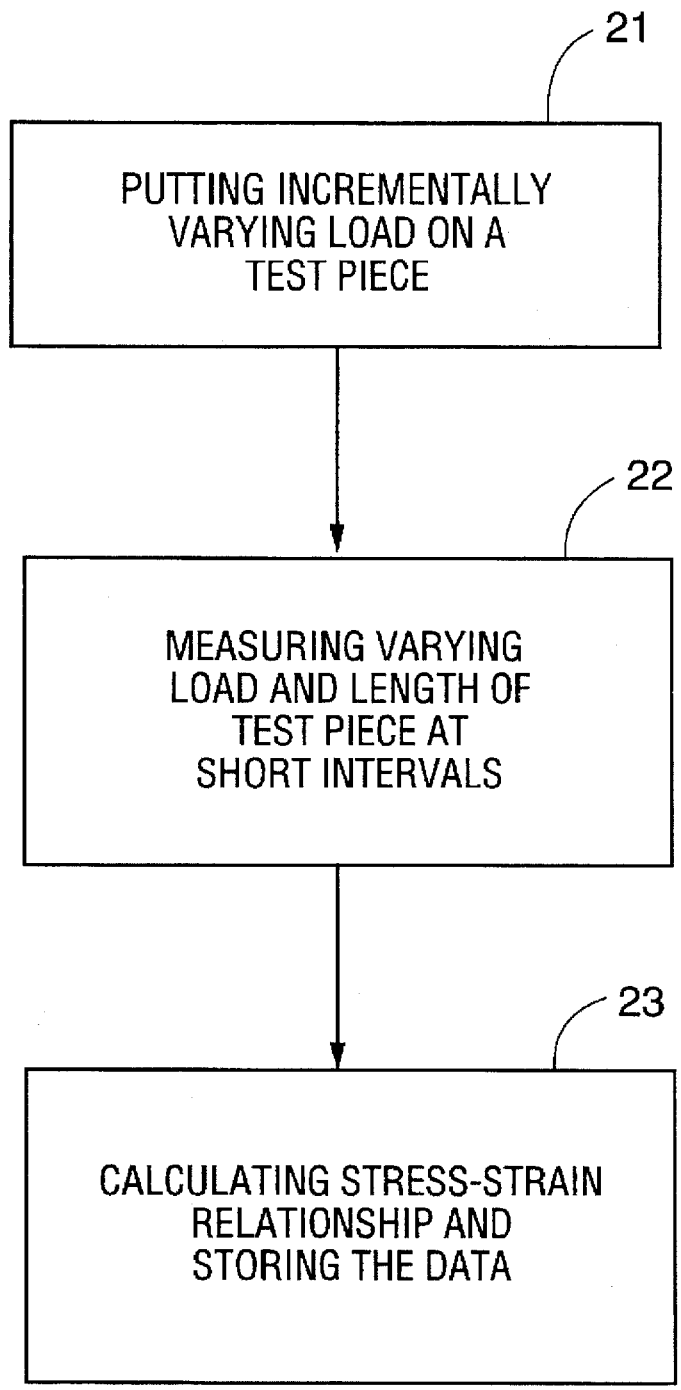
FIG. 1 is a flowchart of the structure of the first aspect of the invention.
Figure 2:
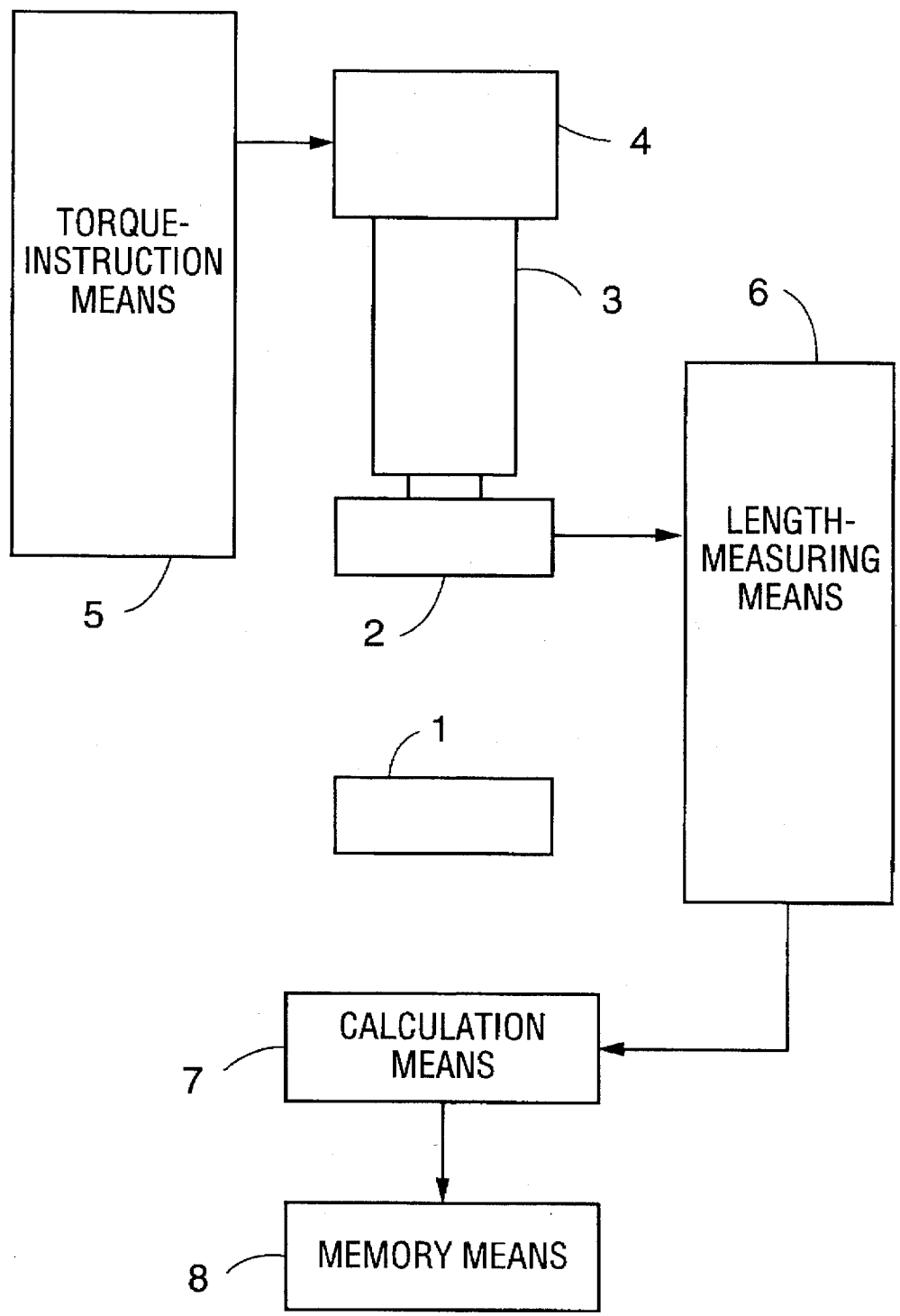
FIG. 2 is a block diagram of the structure of the second aspect of the invention.
Figure 3:
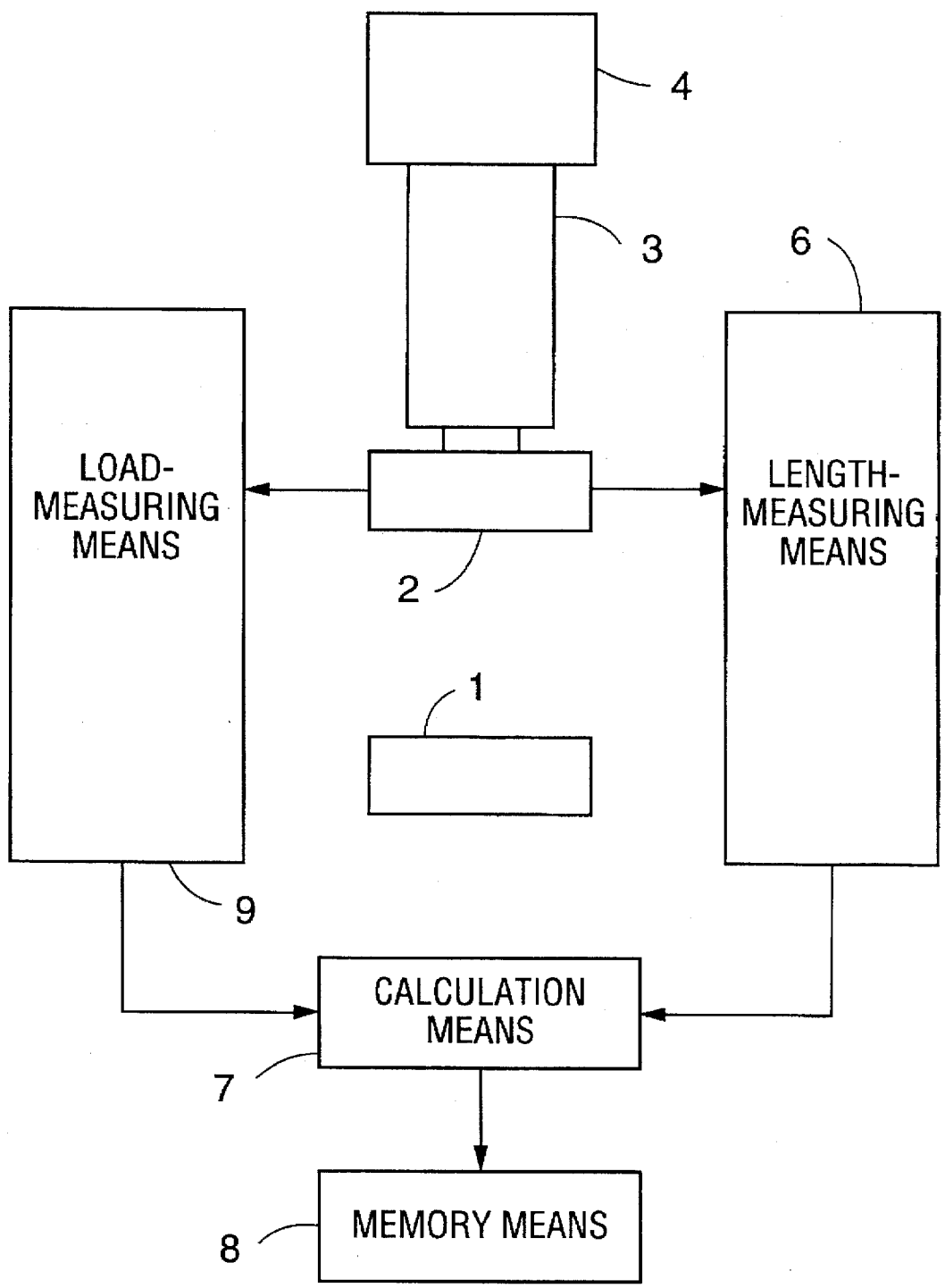
FIG. 3 is a block diagram of the structure of the third aspect of the invention.

The first embodiment of the invention will now be explained by referring to FIG. 4. A table 1, which acts as a first supporting member to support a test piece T, is disposed at the lower central part of a supporting frame 11. An electric cylinder 12, which includes a servomotor 4 and ball screw 3, and which is directed downward, is mounted on the frame and above the table 1. The servomotor 4 is provided with a rotary encoder 13 which acts as a length-measuring means 6. The servomotor 4 is electrically connected to a servo-driver 14 which is in turn electrically connected to a microcomputer 15.

Figure 5:
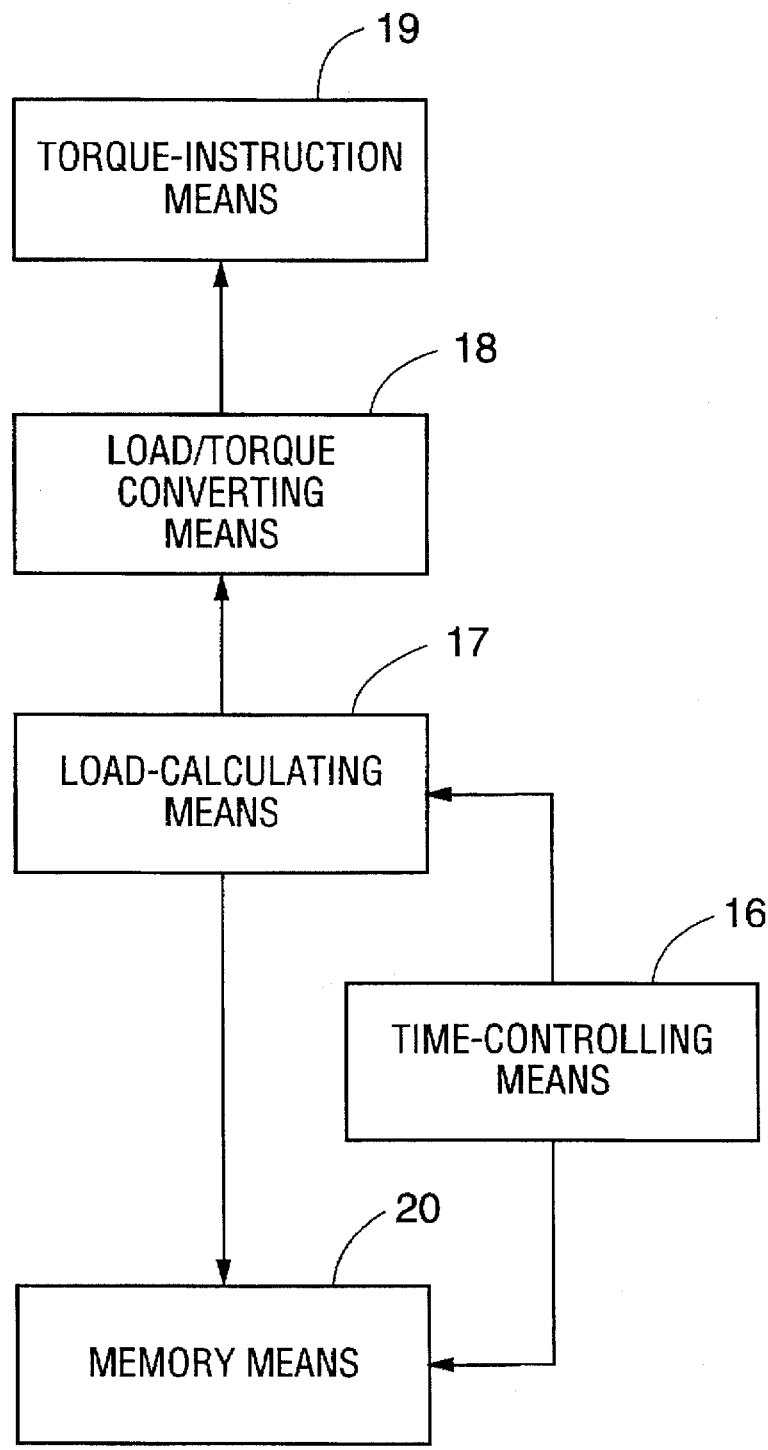
FIG. 5 is a block diagram of the functions of the microcomputer in FIG. 1.

As in FIG. 5, the microcomputer 15 has many functions, such as time-controlling means 16 that control by time the servomotor 4, load-calculating means 17 that calculate the intensity of a load put on the test piece T, load/torque converting means 18 that convert a force resulting from the calculation of the load-calculating means 17 into a torque of the servomotor 4 so that it can output the torque, torque-instruction means 19 that instruct the servo-driver 14 to output a necessary torque based on the result of the conversion of the torque-instruction means 19, and memory means 20 that store the degree of deformation of the test piece detected by the rotary encoder 13 and the intensity of the load measured at short intervals.

Figure 4:
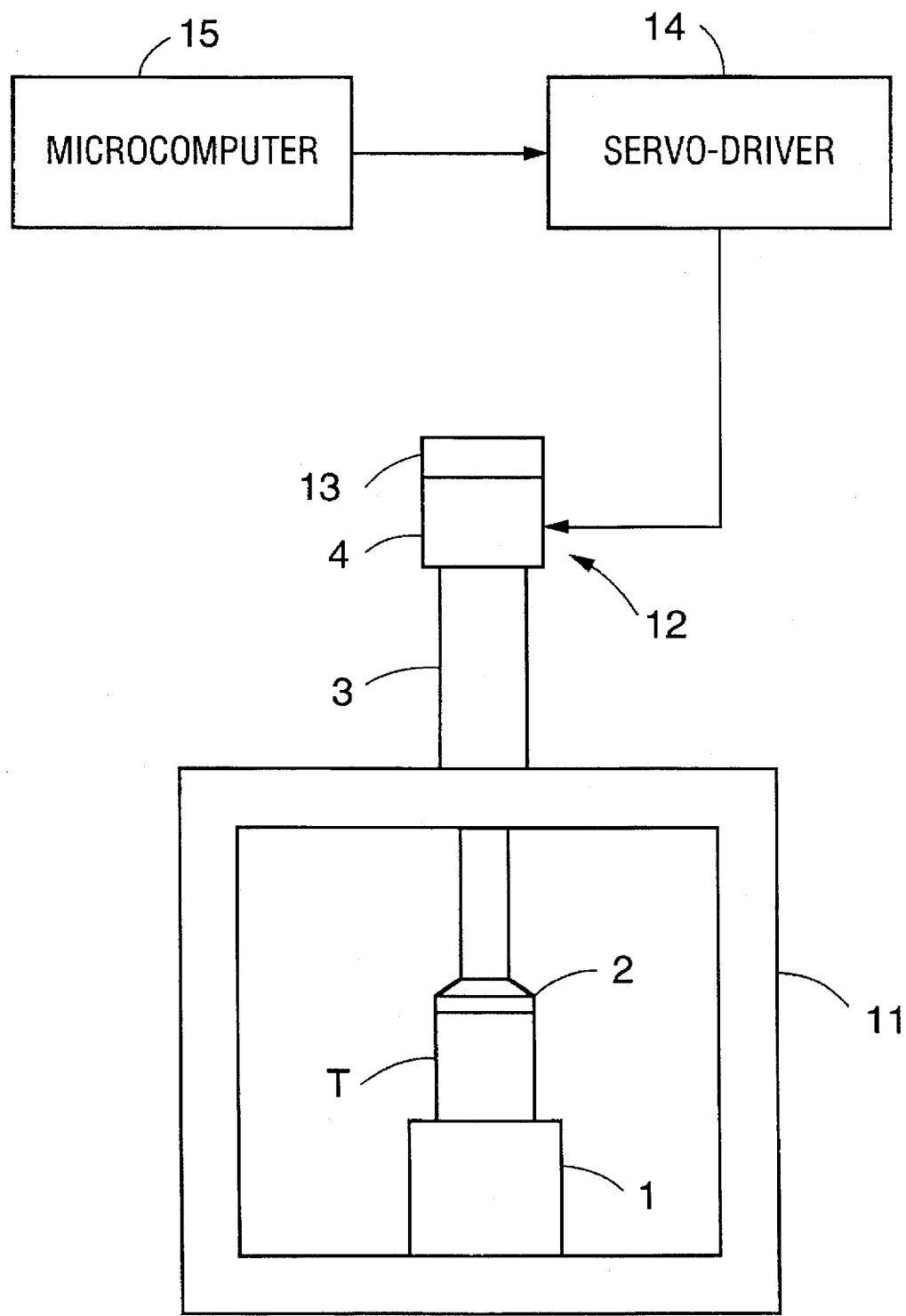
FIG. 4 is a schematic drawing of the first embodiment of the present invention.

Further, as in FIG. 4, a second supporting member 2, which acts as a member to impart a load to the test piece, is secured to the lower end of the screw of the electric cylinder 12.

The operation of the apparatus will now be explained. First, a test piece T is manufactured by compressing molding sand for a green sand mold under conditions approximating those for actually producing a given green sand mold. The test piece is then set on the table 1, and the apparatus is then driven. Accordingly, the servomotor 4 of the electric cylinder 12 is driven to lower the load member 2. This member 2 presses the test piece T. The compression of the test piece T is carried out per JIS (Japanese Industrial Standards) specification S Z 2604 for testing molding sand, where the incremental rate of the load put on the test piece is 0.3 N/cm$^2$ (this expression comes from JIS 2601, 1993 Edition).

Figure 6:
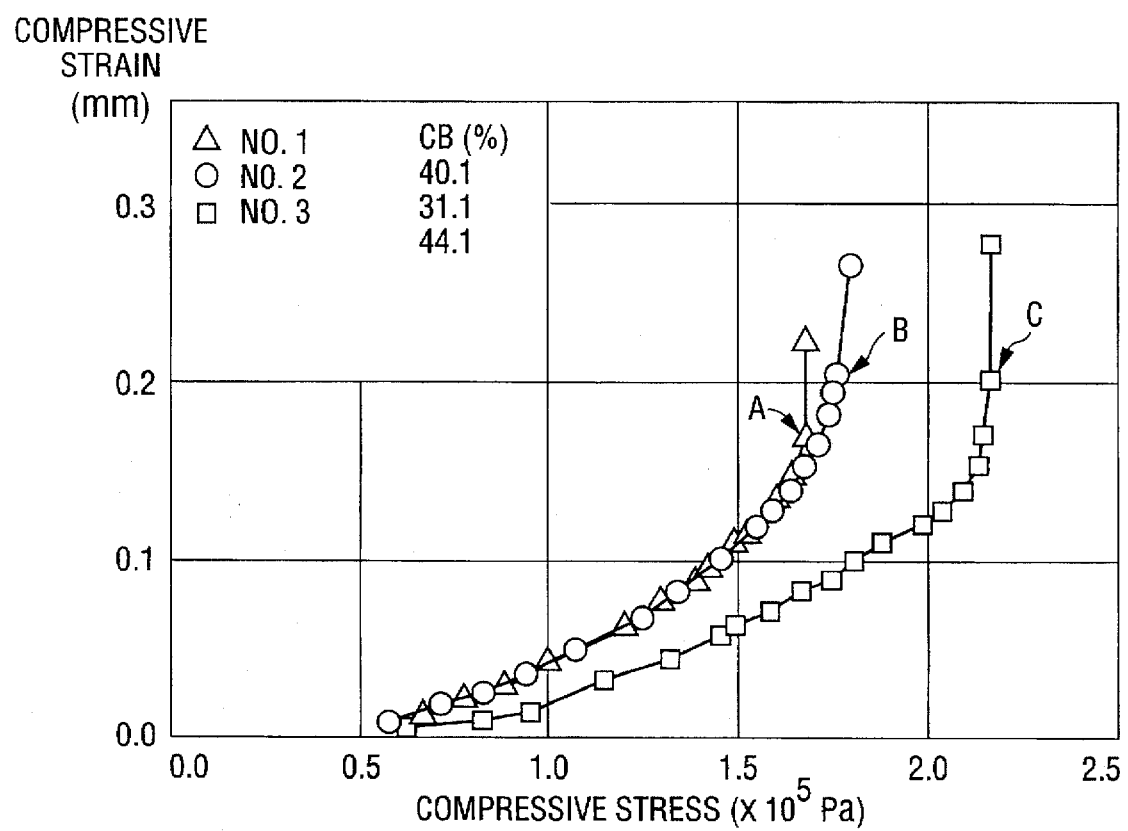
FIG. 6 is a graph obtained by the present invention, of the strain-stress relation of a test piece when it is loaded.

After the load member 2 moves downward and contacts the test piece T, the servo-driver 14 is actuated by the torque instruction of the microcomputer 15, and over time the load on the load member 2 increases. The varying load, and the variation of the length of the test piece T due to it, are measured by the rotary encoder 12 at each interval. Based on the measurements the strain-stress relation of the test piece at each interval is calculated by the microcomputer 15 and then the data is stored. The stored data of the strain-stress relation is shown in FIG. 6, which shows the results of the tests on three samples of molding sand. Points A, B, C indicate the respective limits of deformation on the three tests. Accordingly, by reviewing FIG. 6 the deformation of green sand molds produced from the same molding sand used for the tests is predicted.

Figure 7:
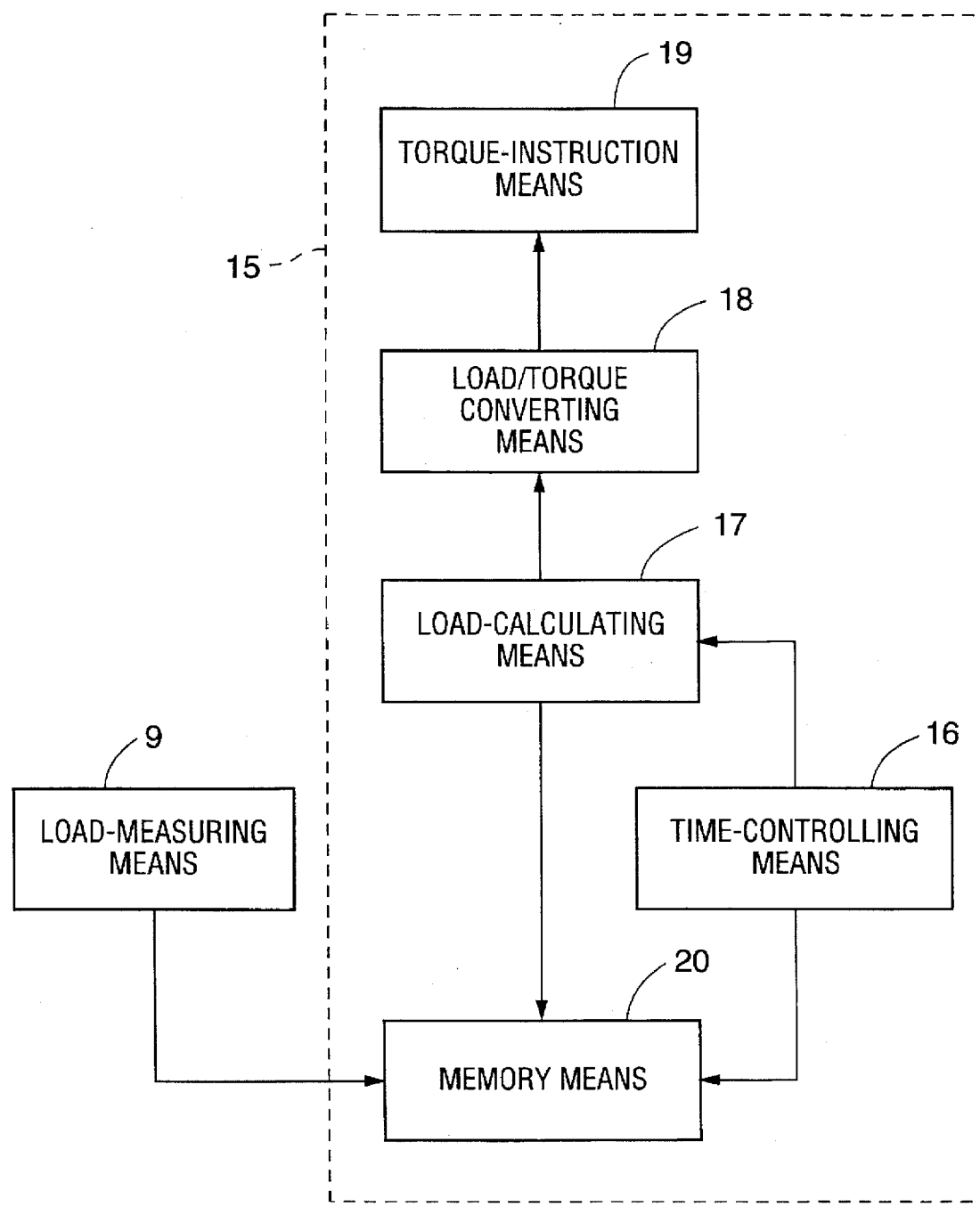
FIG. 7 is a block diagram of the functions of the microcomputer in the second embodiment of the present invention.

In the first embodiment mentioned above the load applied to the test piece T is indirectly measured, but the intensity of the output of the servomotor 4 is used as the load applied to the test piece T. However, this structure may be substituted by one in a second embodiment, as in FIG. 7. In the second embodiment, the electric cylinder 12, for example, may be disposed at the lower part of the frame 11 with the screw rod and the load member 2 facing up. In this case a load cell may be placed on the load member 2 as a load-measuring means 9. Thus the load applied to the test piece T is measured by the load cell while it is compressed. This configuration is effective where the ball screw 3 and/or any other mechanism imparts frictional resistance to the servomotor 4.

Further, in the second embodiment the output signal from the load cell is sent to the microcomputer 15 and the data on the strain-stress relation at each interval is calculated and stored.

In the first and second embodiments a compressive load is applied to the test piece T. However, instead of this, a tensile load may be applied to it by holding and pulling it in a suitable way. Although in the first and second embodiments the intensity of the load is varied by changing the torque of the servomotor 4, instead, this intensity of the load may be varied by changing the electric current supplied to it.

As is seen from the above description, in this invention an incremental load is applied over time to the test piece; the varying load and the variation of the length of the test piece due to the varying load are measured at short intervals; and based on the measurements the data on the strain-stress relation, at short intervals, of the test piece under the varying load, is calculated and stored. Thus the invention enables one to obtain the properties of a green sand mold based on the stored data and to predict the deformation of the green sand mold which may be caused when the mold is moved or filled with molten metal, thereby enabling the deformation to be considered in advance. Thus, it becomes possible to cope with the movement of the green sand mold or its deformation by filling molten metal readily and properly, which is a remarkable advantage of this invention hitherto not attainable.

What we claim is:

1. A method for predicting the degree of deformation of a green sand mold to be moved and filled with molten metal comprising the steps of:

producing a test piece from molding sand that is used to produce the green sand mold, under conditions approximating those for actually producing the green sand mold;

putting on the test piece an incrementally varying load which increases over time;

measuring at short intervals the varying load and the varying length of the test piece under the varying load;

calculating the strain-stress relation of the test piece based on the measurements at such intervals;

storing data indicative of the calculated strain-stress relation; and predicting the degree of deformation of the green sand mold produced from the molding sand from the stored data indicative of the calculated strain-stress relation.

* * * * *